(12) United States Patent
Goshgarian

(10) Patent No.: US 8,226,700 B2
(45) Date of Patent: Jul. 24, 2012

(54) DUAL GUIDE-WIRE MEDICAL DEVICE AND METHOD

(75) Inventor: Justin G. Goshgarian, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 1700 days.

(21) Appl. No.: 10/427,351

(22) Filed: Apr. 30, 2003

(65) Prior Publication Data

US 2004/0220606 A1    Nov. 4, 2004

(51) Int. Cl.
*A61F 2/84* (2006.01)

(52) U.S. Cl. ...................................... 623/1.11

(58) Field of Classification Search .............. 600/585; 606/194, 108, 200; 623/1.11, 1.23; 24/21, 24/26–28, 30.5 T, 30.5 W; 604/164.13; 433/22
See application file for complete search history.

(56) References Cited

U.S. PATENT DOCUMENTS

| | | | | |
|---|---|---|---|---|
| 3,426,393 A | * | 2/1969 | Mead | 24/30.5 T |
| 4,013,085 A | * | 3/1977 | Wright | 132/323 |
| 4,529,636 A | * | 7/1985 | Olson | 428/41.7 |
| 4,655,233 A | * | 4/1987 | Laughlin | 132/323 |
| 4,807,752 A | * | 2/1989 | Chodorow | 206/63.5 |
| 4,876,132 A | * | 10/1989 | Kunert | 428/43 |
| 4,941,488 A | * | 7/1990 | Marxer et al. | 132/323 |
| 5,086,792 A | * | 2/1992 | Chodorow | 132/323 |
| 5,161,533 A | * | 11/1992 | Prass et al. | 600/372 |
| 5,896,867 A | * | 4/1999 | McGaha et al. | 132/321 |
| 6,086,611 A | | 7/2000 | Duffy et al. | |
| 6,117,117 A | * | 9/2000 | Mauch | 604/284 |
| 6,129,738 A | | 10/2000 | Lashinski et al. | |
| 6,428,567 B2 | | 8/2002 | Wilson et al. | |
| 6,475,208 B2 | | 11/2002 | Mauch | |
| 2002/0055732 A1 | * | 5/2002 | Wilson | 604/528 |
| 2002/0085828 A1 | * | 7/2002 | McGarvey | 385/147 |
| 2002/0111675 A1 | | 8/2002 | Wilson | |
| 2002/0173819 A1 | * | 11/2002 | Leeflang et al. | 606/200 |

FOREIGN PATENT DOCUMENTS

| | | |
|---|---|---|
| EP | 0965311 | 12/1999 |
| WO | 02068012 | 9/2002 |

* cited by examiner

*Primary Examiner* — Ryan Severson

(57) ABSTRACT

Methods and apparatus are provided for inserting a moveable device into a channel such as a vein or artery. The apparatus comprises first and second guide-wires joined by multiple breakable bonds for initially retaining portions of the guide-wires in substantially fixed mutual relationship, the multiple bonds breaking as the moveable device advances along the guide wires. The method comprises inserting the dual guide-wire assembly in the channel with the dual guide-wires initially in fixed relationship to each other and separating the guide-wires by advancing the moveable device along the dual guide-wire assembly sequentially breaking the multiple bonds joining the guide-wires. When the last bond between the wires is broken, the distal tips of the guide-wires are released. The arrangement is especially useful for placing dilation balloons with (or without) stents in bifurcated blood vessels.

20 Claims, 8 Drawing Sheets

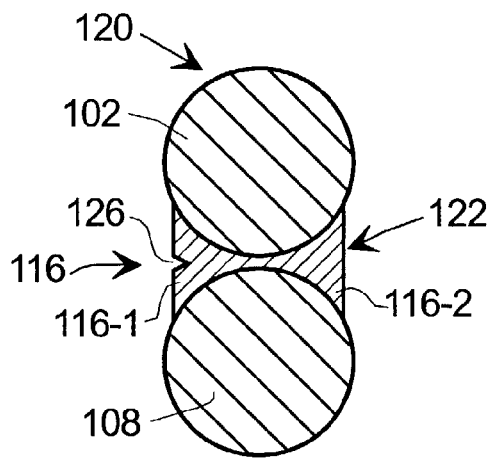
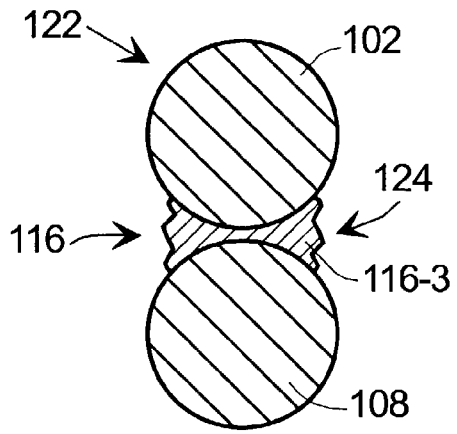
FIG. 6A  FIG. 6B
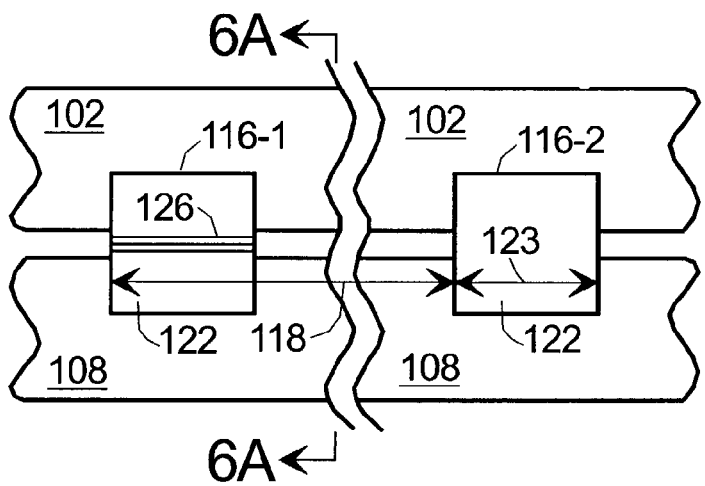
FIG. 5A
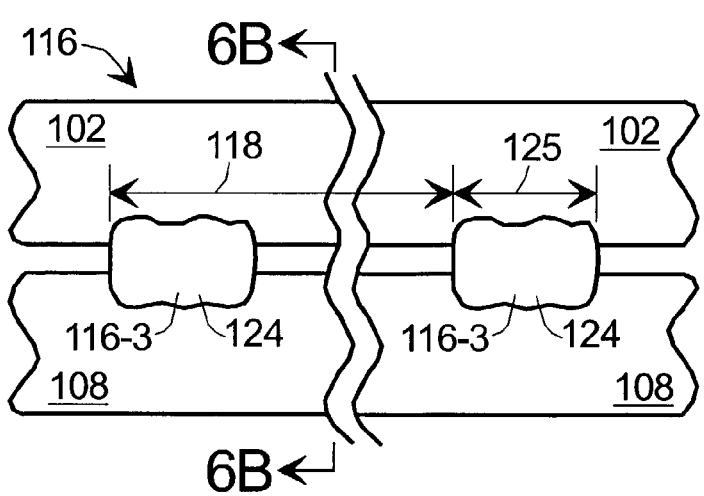
FIG. 5B

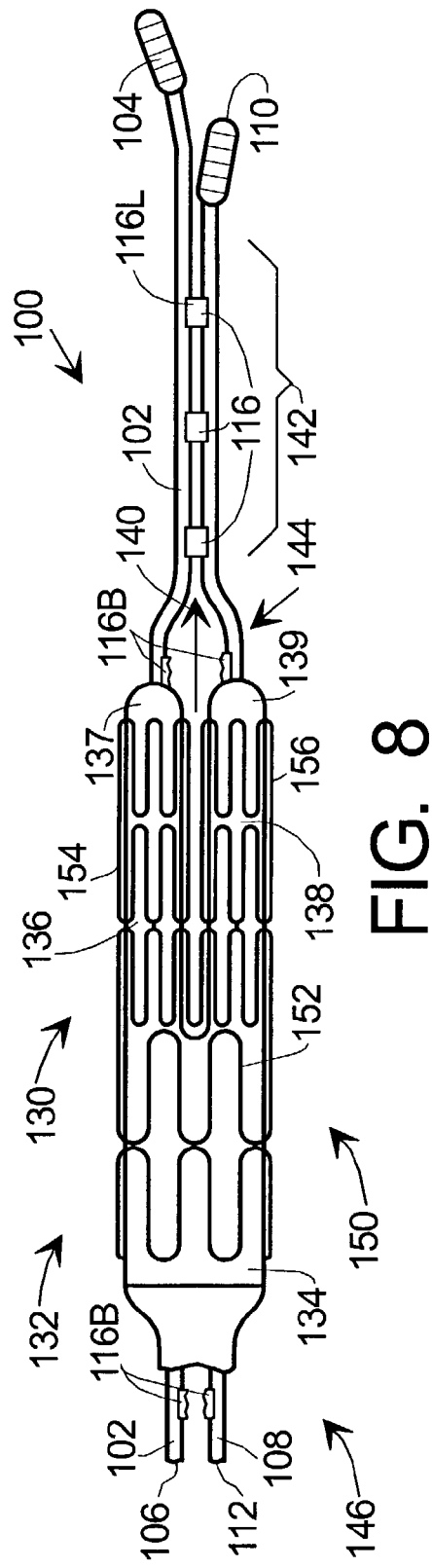
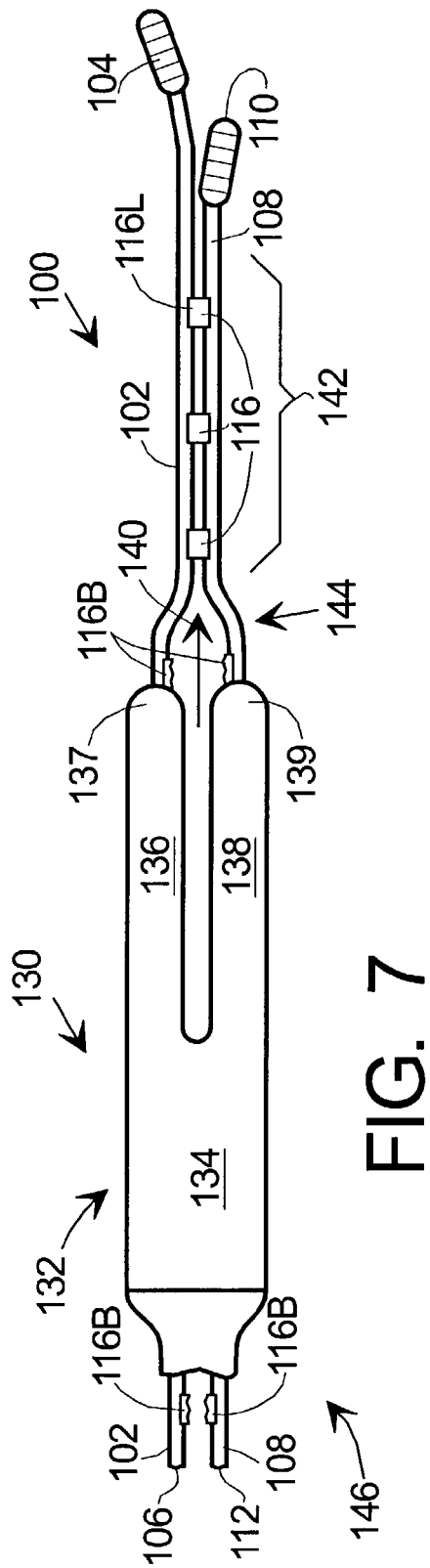
FIG. 7
FIG. 8

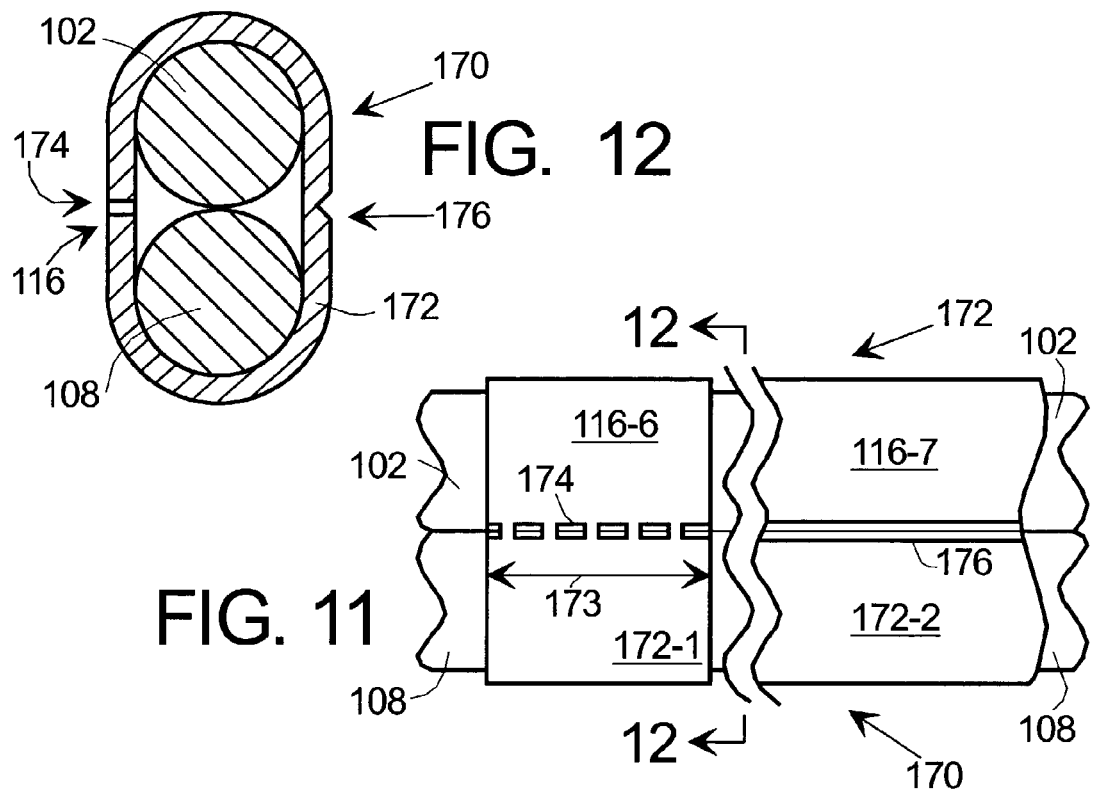
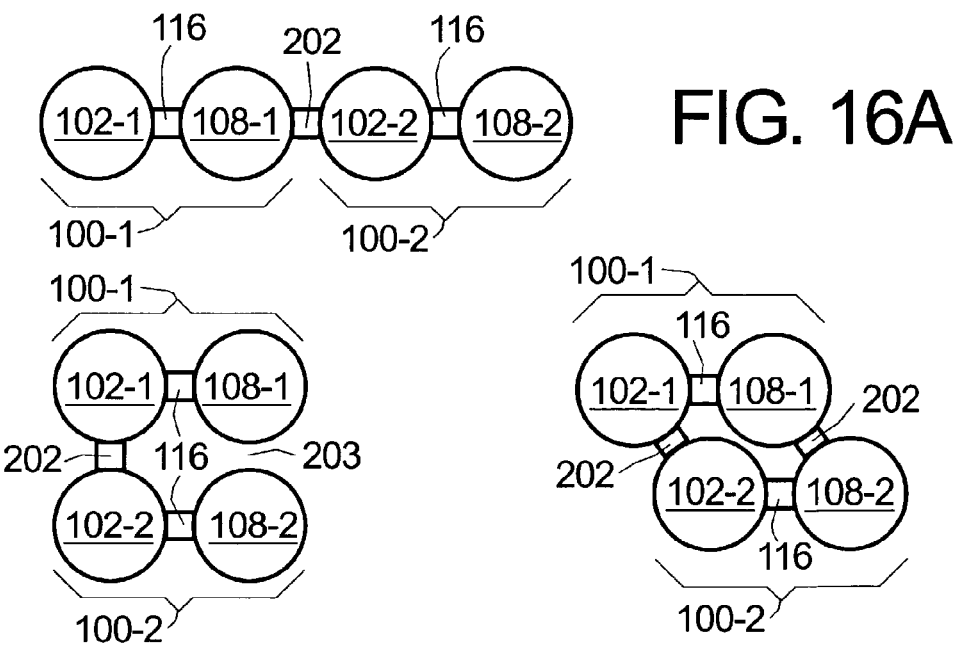

DUAL GUIDE-WIRE MEDICAL DEVICE AND METHOD

TECHNICAL FIELD

The present invention generally relates to means and methods for treatment of partially blocked veins and arteries, and more particularly to improved means and methods for the insertion of bifurcated dilatation balloons and stents.

BACKGROUND

Dilatation balloons and stents are widely used for the treatment of vascular disorders where partial occlusion of a vein or artery has occurred, for example, from a buildup of plaque or other deposits on an inner wall of a blood vessel. Typically a catheter is moved through the blood vessel from a convenient external entry point to the affected region of the vessel. A guide wire and dilatation balloon are inserted in the catheter and advanced through the catheter and blood vessels to the site. Once in position, the flexible, expandable, preformed dilatation balloon is inflated to a predetermined size with a liquid or gas at relatively high pressures (e.g. about eight to twelve atmospheres) to radially compress the arthrosclerotic plaque in the lesion against the inside of the artery wall and thereby dilate the lumen of the artery. The balloon is then deflated to a small profile so that the dilatation balloon, guide-wire and catheter may be withdrawn from the patient's vasculature and blood flow resumed through the dilated artery.

In order to prevent or reduce restenosis; i.e., a natural re-narrowing of the treated artery, an intravascular prosthesis generally referred to as a stent can be implanted in the affected region. The stent often takes the form of a cylindrically shaped, radially expandable mesh fabricated of, for example, stainless steel or other suitable alloy. The stent is inserted by mounting it in collapsed form over a dilatation balloon, advancing the balloon-stent combination along a guide-wire to the site, and then expanded the balloon and the stent so that the stent is pressed into the inner wall of the blood vessel. The stent overcomes the natural tendency of the vessel walls of some patients to close back down. In this way, normal flow of blood is maintained through the vessel that would not be possible if the stent was not in place. Such procedures and stents are generally known in the art.

A particularly difficult problem arises when the blood vessel region to be treated involves a bifurcation, that is, where a single blood vessel divides into two branches. It is much more difficult in this situation to position the dilatation balloon and the stent. Further, where both branches of the bifurcation have plaque deposits, great care must be taken to compress the deposits in both branches as simultaneously as possible to prevent narrowing or closing of one branch while treating the other.

FIG. 1 shows bifurcated blood vessel region 10 with main vessel portion 12 and branches 14, 16. A balloon catheter (not shown) has previously been used to compress plaque 18 present in the bifurcation region against inner walls 20, 22, 24 of vessels 12, 14, 16 respectively. Stent 26 has been brought to the bifurcation region and expanded against compressed plaque 18 on the inner wall of vessels 12, 14, 16. Stent 26 is bifurcated, that is having portion 28 located in main vessel 12, portion 30 located in branch vessel 14 and portion 32 located in branch vessel 16. Thus, stent 26 can reduce or delay restenosis.

A number of catheter assemblies, methods and stents for treating stenosis in bifurcated regions have been described, for example, in U.S. Pat. No. 6,086,611 to Duffy et al; U.S. Pat. No. 6,129,738 to Lashinski et al; U.S. Pat. No. 6,428,567 to Wilson et al; and U.S. Pat. No. 6,475,208 to Mauch. FIGS. 2-3 illustrate prior art dilatation balloon-stent assemblies 40, 80 used in the prior art to place bifurcated stents. In FIGS. 2-3, balloon-stent assemblies 40, 80 have dilatation balloon 42 with main vessel portion 44 and branch portions 46, 48. Dilatation balloon 42 is shown un-inflated with stent 50 mounted thereon, ready for insertion. Stent 50 has main vessel portion 52 and branch portions 54, 56 located, respectively on balloon portions 44 and 46, 48. Running through dilatation balloon 42 are guide-wires 58, 60 where guide-wire 58 passes through dilatation balloon branch 46 and guide-wire 60 passes through dilatation balloon branch 48. One or both of rounded tips 62, 64 on guide-wires 58, 60 are often placed at a slight angle to the guide-wire to facilitate penetration into the branch vessel.

Assembly 80 of FIG. 3 differs from assembly 40 of FIG. 2 in that balloon branch 48 has extension portion 66 attached to distal end 49 thereof and clip 68 provided thereon. Portion 58-1 of guide-wire 58 is initially bent down and placed in clip 68 before insertion of assembly 80 through the catheter (not shown) into the affected region of the blood vessel. This aids in keeping branches 46, 48 of balloon catheter 42 together during insertion, reducing the chance that tip 62 will snag on an interior wall of the vessel or go into a branch ahead of the site being treated. Once assembly 80 is just in front of the bifurcation, guide-wire 58 is withdrawn slightly until it pops out of clip 68, so that assembly 80 now takes on an orientation much like assembly 40 in FIG. 2 as far as tips 62, 64 are concerned. Guide-wires 58, 60 are then advanced respectively into the bifurcated vessel branches. Then balloon catheter portions 46, 48 with stent portions 54, 56 are advanced along guide-wires 58, 60 to place the balloons and respective stent portions into the vessel branches. Balloon 42 is inflated to expand stent 50 and place it against the inner walls of the vessels. Balloon 42 is then deflated and withdrawn. Stent 50 remains in place.

While the above-described apparatus and methods are useful, they suffer from a number of disadvantages. For example, it is often very difficult to advance the dilatation balloon along the guide-wires when the guide-wires become twisted or tangled during insertion. When this happens it is often necessary to withdraw the guide-wires partially or completely and re-insert them. The more the guide-wires and/or balloon assembly are inserted, withdrawn and re-inserted before or after balloon dilatation, the greater the likelihood of damaging the interior wall of the vessel. Damage can occur when one or both of tips 62, 64 and/or stent 50 snag on the vessel wall and/or go into a dissection, that is, a fissure in the vessel wall that can arise from the dilatation process. Further, the need to partially withdraw and advance one or more guide-wires to release tips 62, 64, as for example, with the arrangement of FIG. 3, can exacerbate this situation. In addition, the very large ratio of length L to diameter D of the guide-wires (typically $L/D=10^3$ to $10^4$) means they have very low stiffness, which makes it to difficult to insert them, to control their orientation and to avoid tangling. An increase in stiffness without loss of flexibility is desirable.

Accordingly, there continues to be a need for improved means and methods for dilatation balloons and stents to treat vascular stenosis. In particular, there is an ongoing need for means and methods that reduce the need for withdrawing and re-inserting guide-wires, dilatation balloons and/or stents. Further, there is a need for improved means and methods for treating bifurcated regions so that the guide-wire tips can be maintained in fixed relationship to each other during insertion without requiring one or both to be partially withdrawn in order to be released. In addition, there is an ongoing need for means and methods that reduce twisting and/or tangling of the guide-wires during insertion and manipulation of the dilatation balloon and stent. Furthermore, other desirable features and characteristics of the present invention will become apparent from the subsequent detailed description and the appended claims, taken in conjunction with the accompanying drawings and the foregoing technical field and background.

BRIEF SUMMARY OF THE INVENTION

Methods and apparatus are provided for inserting a medical device into a channel such as a vein or artery, especially one containing a bifurcation. In a preferred embodiment, the medical device comprises a dilatation balloon with or without a stent thereon. The apparatus comprises first and second guide-wires joined by multiple breakable bonds for initially retaining portions of the guide-wires in substantially fixed relationship. The multiple bonds break as the medical device advances along the guide wires toward the distal ends located proximate to the channel bifurcation. When the last bond between the guide-wires is broken, the distal tips of the guide-wires are released and available to guide insertion of, for example, the dilatation balloon (without or without a stent) into the bifurcated region of a vein or artery. The method comprises inserting the dual guide-wire assembly in the channel with the dual guide-wires initially in held fixed relationship to each other by the multiple bonds and separating the guide-wires by advancing the medical device along the dual guide-wire assembly sequentially breaking the multiple bonds joining the guide-wires. In a preferred embodiment, each guide wire passes through a separate branch of the dilatation balloon and guides such branch into the bifurcation channels.

BRIEF DESCRIPTION OF THE DRAWINGS

The present invention will hereinafter be described in conjunction with the following drawing figures, wherein like numerals denote like elements.

FIGS. 5A-B are simplified side views of a portion of the dual guide-wire assembly of FIG. 4 showing further details and according to first and second embodiments of the present invention;

FIGS. 6A-B are simplified cross-sectional views through the guide-wire assembly portion of FIGS. 5A-B, respectively;

FIG. 7 is a simplified side view of a dilatation balloon being advanced along the dual guide-wire assembly of the present invention;

FIG. 8 is a simplified side view similar to FIG. 7 of a dilatation balloon carrying a stent, being advanced along the dual guide-wire assembly of the present invention;

FIG. 11 is a simplified side view of a portion of the dual guide-wire assembly portion of FIG. 4 showing further details and according to a still further embodiment of the present invention;

FIG. 12 is a simplified cross-sectional view through the guide-wire assembly of FIG. 11;

FIGS. 16A-C are simplified schematic illustrations of different guide-wire arrangements for double dual guide-wire assemblies of the present invention.

DETAILED DESCRIPTION

The following detailed description is merely exemplary in nature and is not intended to limit the invention or the application and uses of the invention. Furthermore, there is no intention to be bound by any expressed or implied theory presented in the preceding technical field, background, brief summary or the following detailed description.

Figure 1:
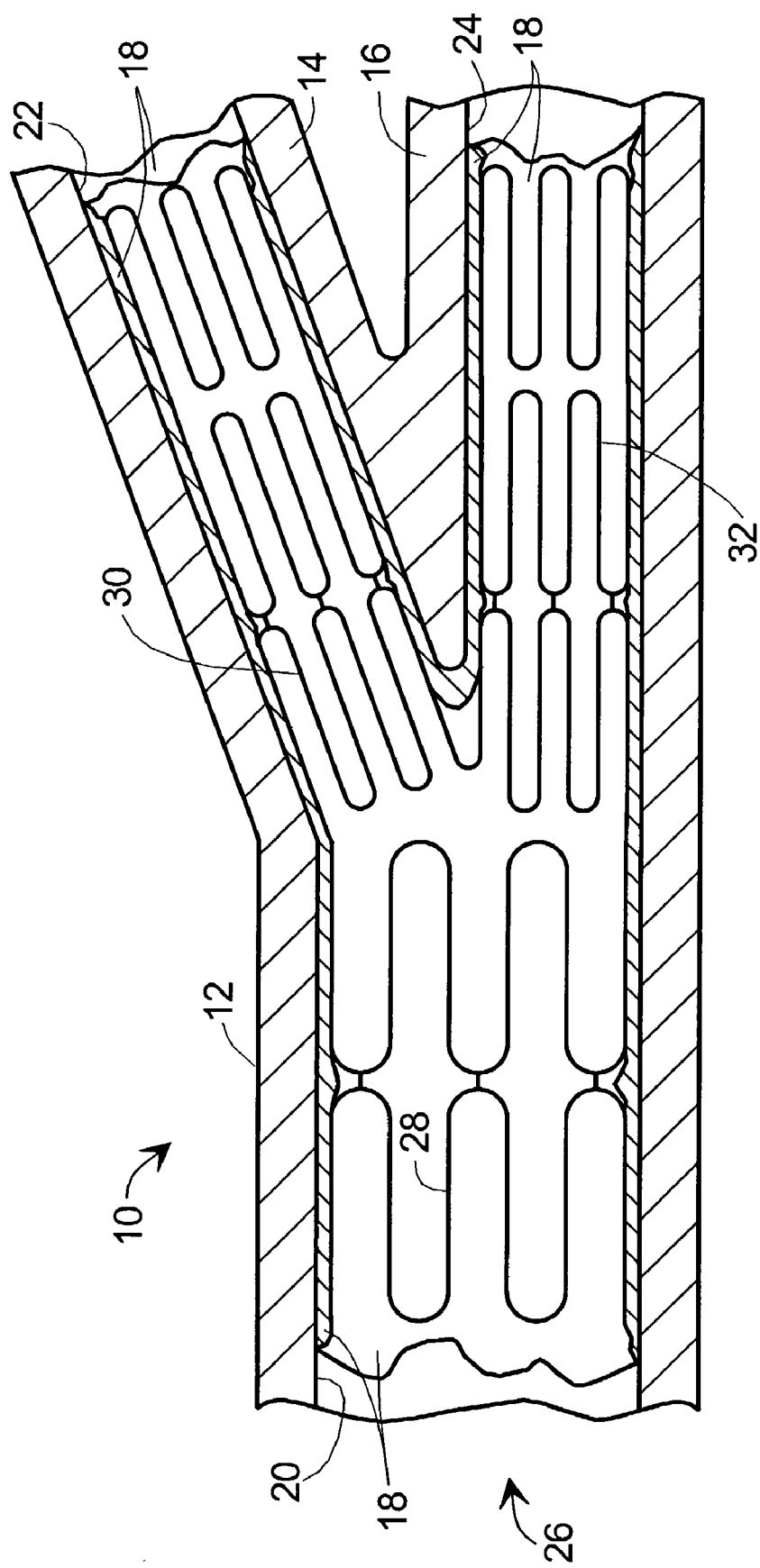
FIG. 1 is a simplified schematic cross-sectional view of a stenotic bifurcated blood vessel in which a stent has been inserted at the bifurcation.
Figure 2:
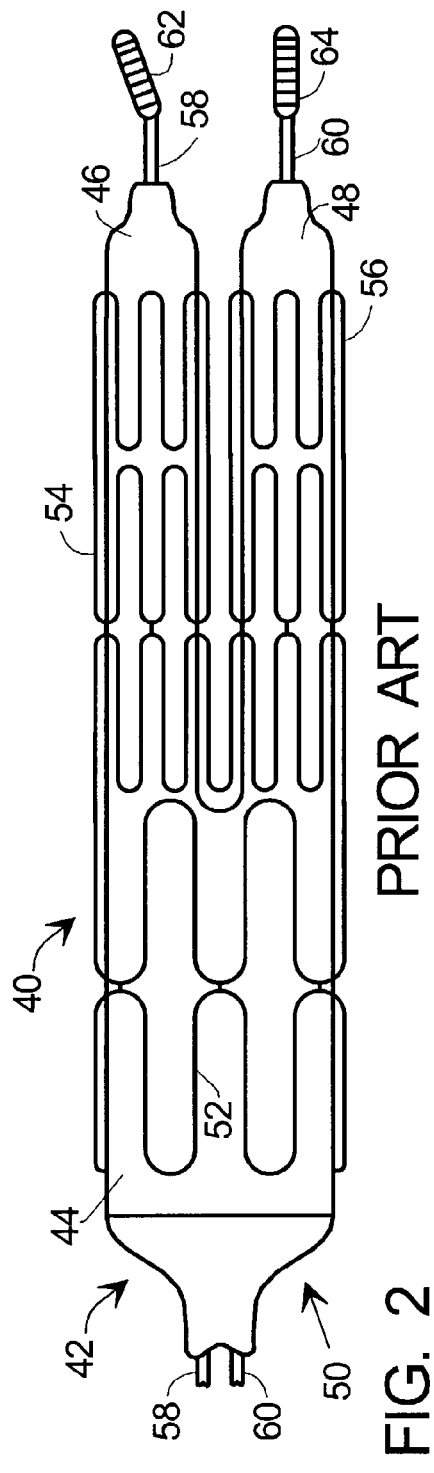
FIG. 2 is a simplified side view of a bifurcated stent delivery assembly according to the prior art.
Figure 3:
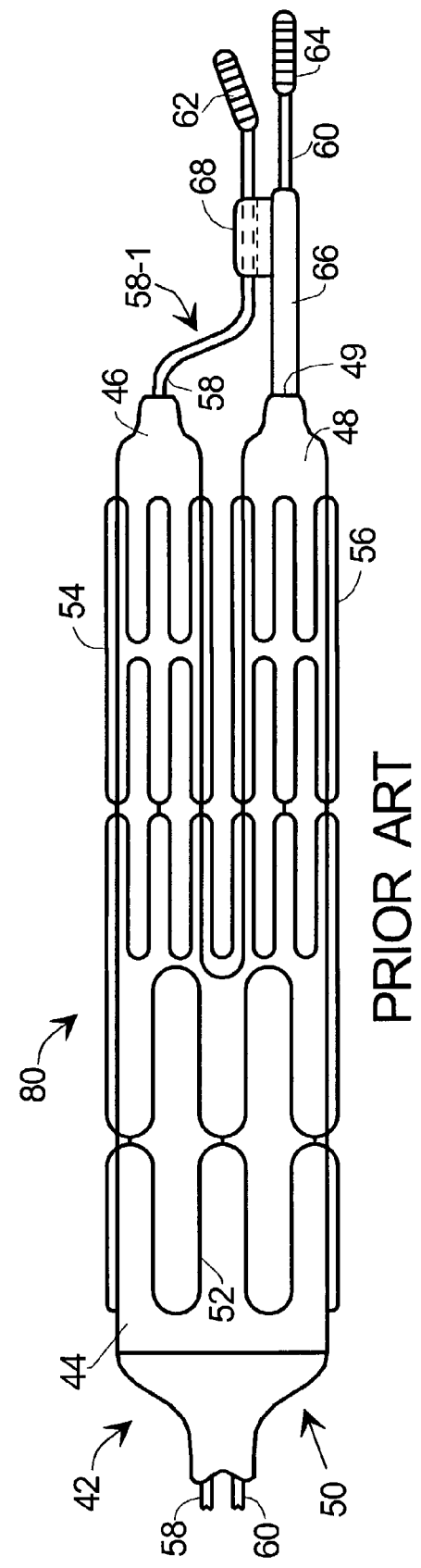
FIG. 3 is a simplified side view similar to FIG. 2 of a further bifurcated stent delivery system according to the prior art.
Figure 4:
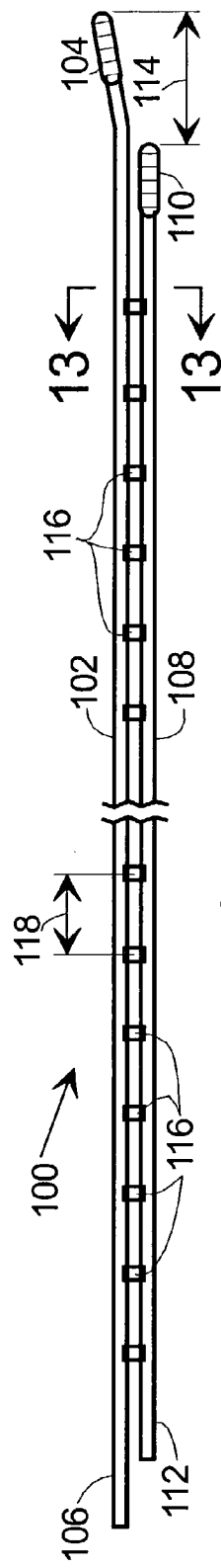
FIG. 4 is a simplified side view of a dual guide-wire assembly for inserting balloon catheters and/or stents, according to the present invention.

FIG. 4 is a simplified side view of dual guide-wire assembly 100 for use with balloon catheters and/or stents, according to the present invention. Assembly 100 has first guide-wire 102 with distal tip 104 and proximal end 106, and second guide-wire 108 with distal tip 110 and proximal end 112. Tips 104, 110 are desirably rounded but any suitable shape may be used. Guide-wires 102, 108 are conveniently of Ni—Ti alloy referred to as NITINOL, with a polymer coating. Such polymer coatings are well known in the art. For example and not intended to be limiting, polyamides, urethanes, PBAC or esters are useful polymer coatings. Guide-wires 102, 108 typically have diameters D on the order of ~0.28 mm uncoated and ~0.36 mm when polymer coated, but larger and smaller diameter wires and wires made of other materials can also be used. Typical guide-wires have lengths L of from 100-500 cm. Tips 104, 106 are staggered by distance 114 of the order of 10-150 mm to facilitate insertion in vessel branches. It is useful to have one or both tips 104, 110 offset at a slight angle with respect to the axis of the respective guide-wire. In FIG. 4, for purposes of illustration and not intended to be limiting, tip 104 is angled and tip 110 is straight.

Guide-wires 102, 108 are breakably joined or bonded together at multiple locations 116. Spacing 118 between bonds or joining locations 116 are between approximately 0-200 mm and conveniently 10-150 mm but, as will be subsequently explained, other spacings and substantially continuous bonding or joining of guide-wires 102, 108 may also be used. It is important that bonds or joining locations 116 be separable or breakable, that is, that guide-wires 102, 108 can be popped apart as a balloon catheter and/or stent are advance from proximal ends 106, 112 toward distal ends 104, 110 in the direction of arrow 140 in FIGS. 7-8.

FIGS. 5A-B are simplified side views of portions 120, 122 of the dual guide-wire assembly 100 of FIG. 4 showing further details and according to first and second embodiments of the present invention. FIGS. 6A-B are simplified cross-sectional views through the dual guide-wire assemblies of FIGS.

5A-B, respectively. FIGS. 5A-B illustrated several spaced-apart joining or bonding regions 116, formed, for example, by applying localized adhesive or adhesive coated connectors 122, 124 between guide-wires 102, 108. Reference numbers 116-1, 116-2, 116-3 . . . etc., are used herein to identify variations in bonding or joining regions 116. In FIGS. 5A-6A, plastic connecting members 122 of width 123 and spacing 118 are, for example, adhesively bonded between guide-wires 102, 108 at locations 116-1, 116-2. Some or all of connecting members 122 are scored by groove or slot 126 to facilitate fracture of connecting member 122 in the manner illustrated in FIGS. 7-8, but this is not essential. For purposes of illustration, members 122 are shown with groove or slot 126 in region 116-1 and without groove or slot 126 in region 116-2 in FIGS. 5A-6A.

FIGS. 5B-6B illustrate use of adhesive 124 to join guide-wires 102, 108 in locations 116-3. Adhesive 124 is conveniently injected or squeezed between guide-wires 102, 108 at locations 116-3. This is readily accomplished by means well known in the art. While adhesive 124 is shown as being applied at distinct locations 116-3 of width 125 and spacing 118, those of skill in the art will understand based on the explanation herein, that spacing 118 and width 125 of adhesive 124 may be varied, even so much that adhesive 124 is applied substantially continuously between guide-wires 102, 108, except at ends 104, 110 and 106, 112. All that is necessary is that guide-wires 102, 108 progressively separate when passed through bifurcated dilatation balloon 132 as shown in FIGS. 7-8. Those of skill in the art will understand that this is accomplished by controlling the amount and nature of adhesive 124. This can be determined without undue experimentation depending upon the type of adhesive and cure method selected. A non-limiting example of a suitable adhesive is LOCTITE®-461, available from the Henkel Loctite Corporation, Rocky Hill, Conn. 06067.

FIG. 7 is a simplified side view of stenosis treatment assembly 130 comprising dilation balloon 132 having main body 134 and branches 136, 138 being advanced along dual guide-wire assembly 100, in the direction of arrow 140. Guide-wires 102, 108 of assembly 100 are still tied together by bonds or joining regions 116 in portion 142 to the right of dilation balloon 132 in FIGS. 7-8, that is, between dilation balloon 132 and distal ends 104, 110. As ends 137, 139 of branches 136, 138 of dilation balloon 132 moves toward guide-wire ends 104, 110, then in transition region 144 guide-wires 102,108 must spread apart to enter the spaced-apart openings in balloon ends 137, 139. This spreading causes bonds or joining regions 1168 near ends 137, 139 to fracture or separate so that each guide-wire 102, 108 can pass through its respective dilation balloon branch 136, 138, through main body 134 and emerge at proximal end 146 of assembly 130. A great advantage of the arrangement of assembly 130 using dual guide-wire assembly 100 is that ends 104, 110 of guide-wires 102, 108 are held in substantially fixed relationship while guide-wires 102, 108 and treatment assembly 130 are being inserted in the vein or artery and maneuvered into position before the bifurcation and aligned therewith. Only when dilation balloon 132 is advanced to the distal end of dual guide-wire assembly 100 does last bond or joining location 116-L break, releasing tips 104, 110. This greatly facilitates insertion and alignment. The arrangement of FIG. 7 can be used to flatten the plaque in the bifurcation region in preparation for placing a stent therein.

FIG. 8 is a simplified side view similar to FIG. 7 of dilatation balloon 132 of FIG. 7 carrying collapsed stent 150, being advanced along dual guide-wire assembly 100 in the direction of arrow 140. The details of dilatation balloon 132 in FIG. 8 are the same as in FIG. 7. Stent 150 has main body portion 152, and branch portions 154, 156 riding on dilatation balloon main body 134 and branches 136, 138, respectively. The explanation given above with respect to FIG. 7 also applies to FIG. 8, and the same advantages obtain. In particular, having dual guide-wire assembly 100 tied together by bonds or joining locations 116 until just before stent 150 is delivered to the bifurcation is a great advantage. When last bond or joining region 116-L reaches region 144 proximate to ends 137, 139 of dilatation balloon 132, bond 116-L breaks or separates thereby releasing tips 104, 110 so that stent 150 may be placed in the bifurcated region.

Figure 10:
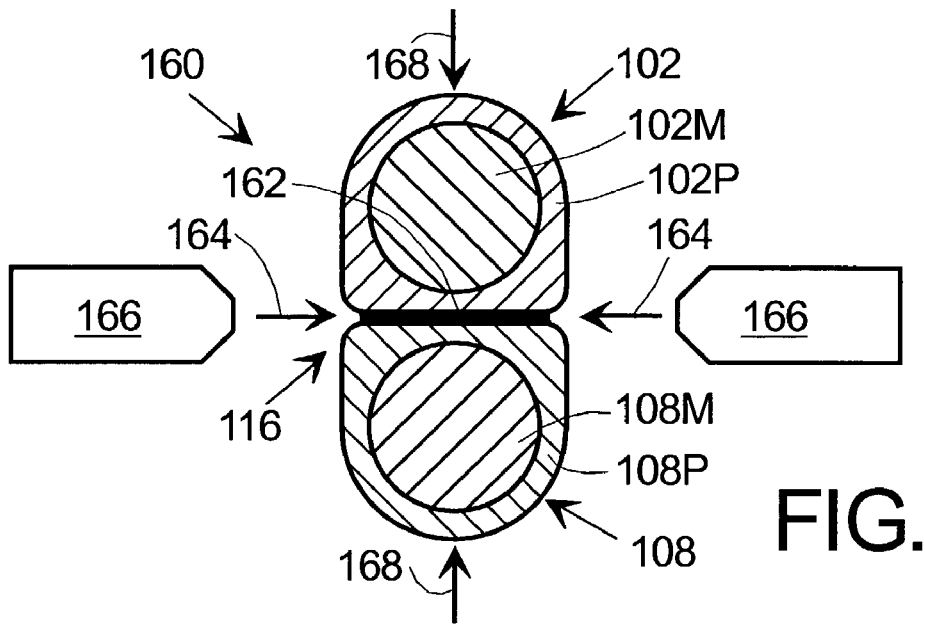
FIG. 10 is a simplified cross-sectional view through the guide-wire assembly of FIG. 9.
Figure 9:
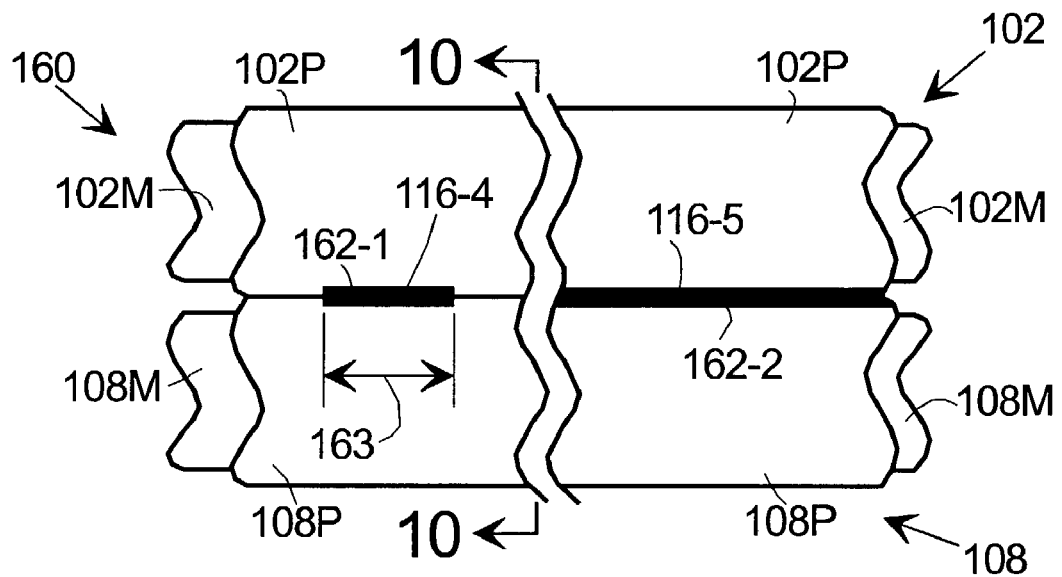
FIG. 9 is a simplified side view of a portion of the dual guide-wire assembly portion of FIG. 4 showing further details and according to a further embodiment of the present invention.

FIG. 9 is a simplified side view of portion 160 of the dual guide-wire assembly 100 of FIG. 4 showing further details and according to a further embodiment of the present invention. FIG. 10 is a simplified cross-sectional view through the guide-wire assembly portion of FIG. 9. FIGS. 9-10 show further details of guide-wires 102, 108 whereby guide-wires 102, 108 have central metal cores 102M, 108M and polymer coatings 102P, 108P, as mentioned earlier. Polymer coatings 102P, 108P are fused together in region 162 to provide bonds or joining locations 116. This is conveniently accomplished by, for example, using lasers or other focused energy beams 164 from sources 166 directed at regions 162 while force is applied as denoted by arrows 168. Polymer coatings 102P, 108P on guide-wires 102, 108 desirably have "D-shaped" cross-sections. Wires 102, 108 are arranged in FIGS. 9-10 with the flat sides of the "D" facing each other in proximal relationship. This conveniently increases the surface area where guide-wires 102, 108 are to be bonded together, either locally or continuously or a combination thereof. Metal cores 102M, 108M can be circular with D-shaped varying thickness polymer coatings as illustrated in FIG. 10 or metal cores 102M, 108M can be D-shaped with a substantially uniform thickness polymer coating. Either arrangement is useful. D-shaped guide-wires 102, 108 of either configuration are suitable for use with bonding and joining arrangements illustrated elsewhere herein, e.g., as in FIGS. 4-16.

However, other joining methods may also be used, as for example and not intended to be limiting, applying a small amount of solvent or adhesive or both in regions 162 to soften and locally bond polymer coatings 102P, 108P in response to pressure denoted by arrows 168. Either of these or other methods well known in the art are useful for creating regions 162 serving as bonds or joining locations 116. As illustrated in the left half of FIG. 9, bond or joining location 116-4 formed by regions 162-1 of width 163 and separation 118 (see FIG. 4) is provided. However, such bonds or joining locations 116-4 from regions 162-1 need not be discrete but as illustrated by bond or joining location 116-5 formed by region 162-2 in the right half of FIG. 9, can also be substantially continuous. It is only necessary that assembly 100 using the embodiment illustrated by portion 160 of FIGS. 9-10 separate when dilatation balloon 132 is advanced in the direction of arrow 140 in FIGS. 7-8. Persons of skill in the art will understand based on the description herein that the strength of bonds 116-4, 116-5 can be adjusted by varying the fusion time, power and size of fused region(s) 162 in order to accomplish this.

FIG. 11 is a simplified side view of portion 170 of the dual guide-wire assembly 100 of FIG. 4 showing further details and according to a still further embodiment of the present invention. FIG. 12 is a simplified cross-sectional view through the guide-wire assembly portion of FIG. 11. Portion 170 has wire-guides 102, 108 surrounded by plastic tubing 172. Plastic tubing 172 is preferably shrink-wrap tubing. Shrink-wrap tubing has the property that in its pre-treated state, it has a larger inside diameter and therefore may be easily slipped over combined guide-wires 102, 108. But when heated or otherwise treated, it shrinks to fit closely around the combination of guide-wires 102, 108, thereby holding them firmly together. Shrink-wrap tubing 172 may be applied in discrete portions 172-1 of width 173 and spacing 118 (see FIG. 4) to form bonds or joining locations 116-6 as illustrated in the left-hand portion of FIG. 11, or applied as substantially continuous element 172-2 to form substantially continuous bond or joining location 116-7 as illustrated in the right-hand portion of FIG. 11.

To facilitate plastic tubing 172 breaking apart when dilatation assembly 130 of FIGS. 7-8 advances along dual guide-wire assembly 100 employing arrangement 170, cutouts 174 and/or scoring grooves 176 may be provided. By controlling the wall-thickness of tubing 172 and the frequency, size and depth of cutouts 174 and/or the size and depth of grooves 176, the force required to separate guide-wires 102, 108 using the arrangement of FIGS. 11-12 when placed in the configuration of FIGS. 7-8, may be advantageously controlled. It is desirably that some adhesive be applied between guide-wires 102, 108 and tubing 172 if the arrangement of 116-6 is used in order to prevent the upper and/or lower halves of tubing pieces 172-1 from separating from wires 102, 108 and becoming lodged in the blood vessel being treated. With the arrangement of configuration 116-7 where the tubing is substantially continuous, the separated halves of tubing 172-2 may be withdrawn when the stenosis treatment assembly 130 is withdrawn.

Figure 13:
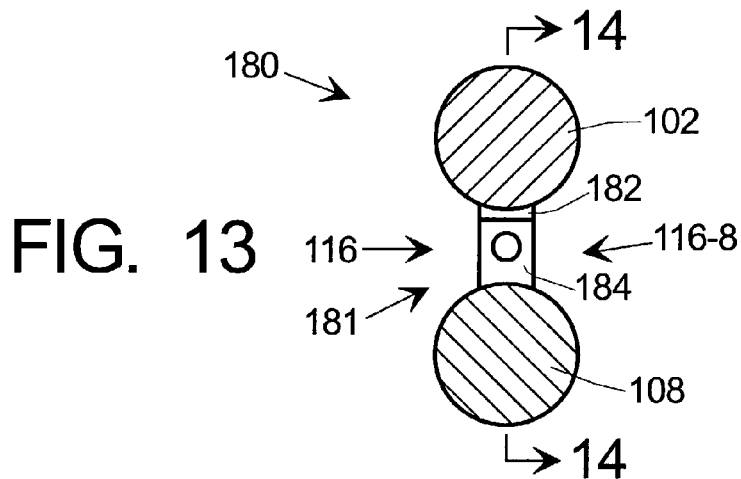
FIG. 13 is a simplified cross-sectional view through the guide-wire assembly of FIG. 4 according to an additional embodiment of the present invention.
Figure 14A:
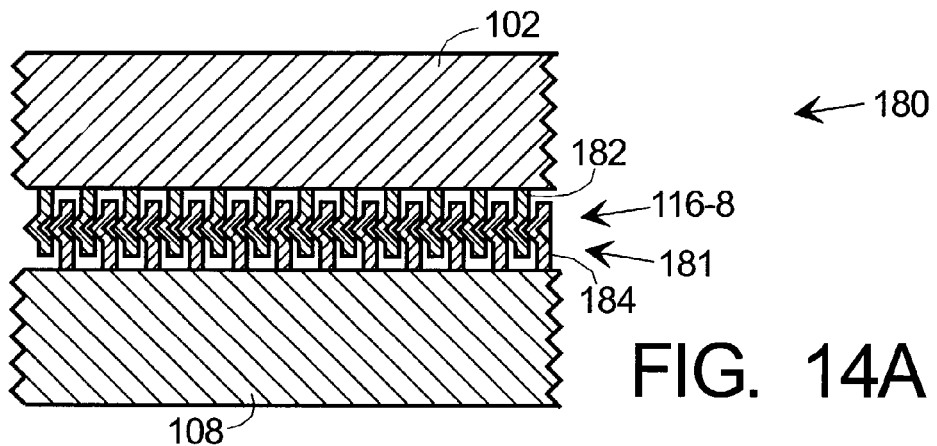
FIGS. 14A-B are simplified cross-sectional views of the dual guide-wire assembly portion of FIG. 13, showing further details.
Figure 14B:
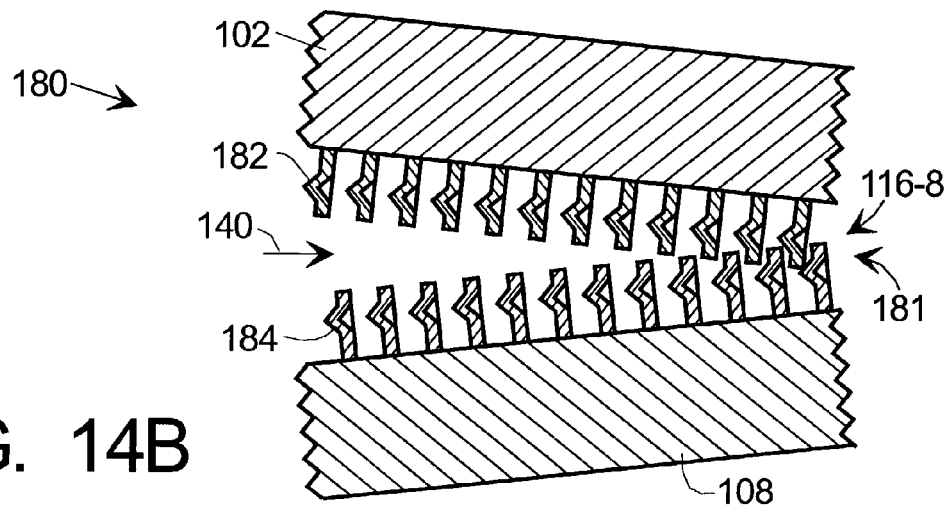

FIG. 13 is a simplified cross-sectional view of guide-wire assembly 100 at location 13-13 of FIG. 4, and FIGS. 14A-B are simplified cross-sectional views taken at right angle to the view of FIG. 13 at location 14-14 of FIG. 13, together showing still further details of wire-guide assembly portion 180 illustrating a still further embodiment of the present invention. Joining location 116 of portion 180 of assembly 104 is referred to by reference number 116-8 to distinguish it from other implementations of joining location 116. Joining location 116-8 is formed by zipper-like structure 181 wherein teeth 182 extend from guide-wire 102 toward guide-wire 108 and teeth 104 extend from guide-wire 108 toward guide-wire 102. Teeth 182, 184 interlock like the teeth of a zipper, as illustrated in FIGS. 14A-B. FIG. 14A shows zipper-structure 181 of joining location 116-8 in the engaged or closed configuration whereby guide-wires 102, 108 are temporarily locked together. FIG. 14B shows the same region as in FIG. 14A but with zipper structure 181 opening as it approaches region 144 in FIGS. 7-8. Thus joining location or means 116-8 employing zipper structure 181 is locally capable of retaining guide-wires 102, 108 in joined configuration, progressively un-zipping as dilatation balloon (with or without stent 150) advances toward distal ends 104, 110, whereupon zipper 181 forming joining location 116-8 fully opens, thereby releasing guide-wires 102, 108 and separating tips 104, 110, as desired. Zipper structure 181 of joining location 116-8 is preferably substantially continuous rather than spaced apart, but this is not essential. Zipper teeth 182, 184 are conveniently formed of metal or plastic and interlock in much the same way as a conventional zipper for joining cloth or other flexible material. Teeth 182, 184 may be attached to guide-wires 102, 108 by any convenient means, as for example but not limited to, welding, gluing, crimping around a longitudinal ridge on guide-wires 102, 108, engaging slots in the ridge or in guide-wires 102, 108, combinations thereof or other suitable means well known in the art.

Figure 15:
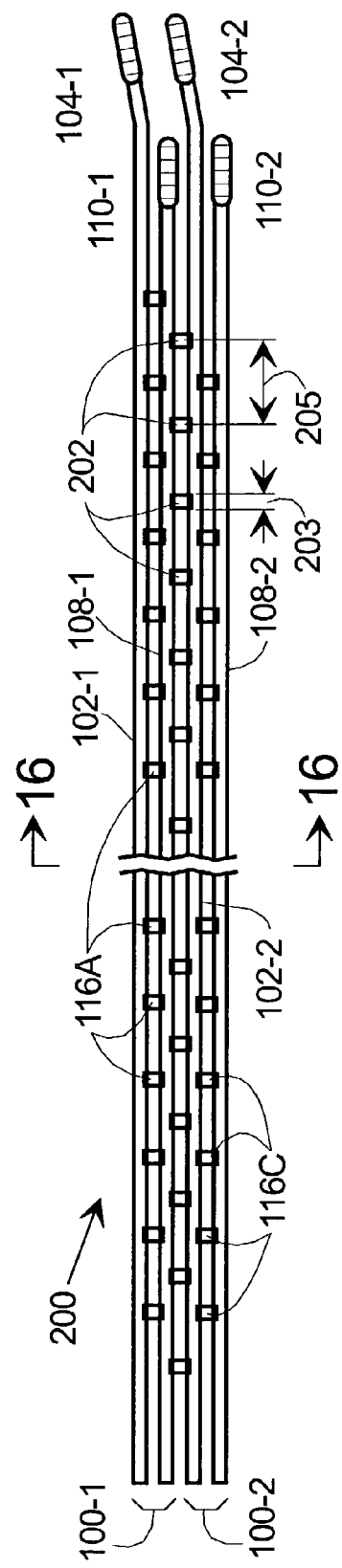
FIG. 15 is a simplified side view, similar to FIG. 4, of a double dual guide-wire assembly according to a yet further embodiment of the present invention.

FIG. 15 is a simplified side view, similar to FIG. 4, but of double dual guide-wire (DDGW) assembly 200 according to a yet further embodiment of the present invention. DDGW assembly 200 is conveniently formed of two dual guide-wire assemblies 100-1, 100-2 constructed according to the principles taught herein. Individual dual guide-wire assemblies 100-1, 100-2 have guide-wires 102-1, 108-1 and 102-2, 108-2, bonds or joining locations 116A, 116C, and tips 104-1, 110-1 and 104-2, 110-2, respectively. Each dual guide-wire assembly 100-1, 100-2 is suitable for use with dilatation balloon 132 with or without stent 150. Dual wire-guide assemblies 100-1, 100-2 are conveniently joined by bonds or joining locations 202 of width 203 and spacing 205 analogous to and made generally in the same way as bonds or joining locations 116 (e.g., 116-1, 116-2, . . . 116-8 or any combination thereof) as described herein.

FIGS. 16A-C are simplified cross-section views through DDGW assembly 200 of FIG. 15, showing alternative arrangements of the guide-wires. For simplicity of illustration, cross-hatching has been omitted. In FIG. 16A, DDGW assembly 200 of FIG. 15 is shown as being substantially flat, that is with the guide-wires 102-1, 108-1, 102-2, 108-2 joined by bonds 116, 202 and lying substantially in a common plane. This corresponds to the arrangement shown in FIG. 15. However, persons of skill in the art will understand based on the description herein, that DDGW assembly 200 may be folded so that dual guide-wire assemblies 100-1 and 100-2 are superposed rather than side-by-side. Such alternative arrangements are illustrated in FIGS. 16B-C. In FIG. 16B, dual guide-wire assemblies 100-1 and 100-2 lie one above the other and bonds 202 attach to guide-wires 102-1 and 102-2 (or 108-1 and 108-2 or both) at right angles to bonds 116. While bonds 202 are shown between wires 102-1 and 102-2, bonds 202 can also be placed in location 203 between guide-wires 108-1 and 108-2 or in both locations. In FIG. 16C, dual guide-wire assemblies 100-1 and 100-2 are located one above the other but laterally displaced so that they fit together more compactly, making it easier to insert them through the catheter and the blood vessel. In FIG. 16C, the use of dual bonds 202 is illustrated, but this is not essential. The arrangements of FIGS. 16A, 16B, 16C are obtained by varying the location of bonds or joining locations 202 around the circumference of the guide-wires.

The advantage of DDGW assembly 200 is that it may be inserted into the blood vessel as a unit. The individual guide-wires of DDGW assembly 200 are much less likely to become twisted or tangled, as may happen when guide-wires are inserted individually. With DDGW assembly 200, one dual guide-wire assembly, e.g., 100-1, can be used with first dilatation balloon 132-1 (e.g., see FIG. 7) to compress the plaque against the inside walls of the vessels. When first dilatation balloon assembly 132-1 is advanced along guide-wire 100-1 it breaks bonds or joining locations 116A and bonds or joining locations 202, leaving second dual guide-wire assembly 100-2 unaffected. After the plaque has been compressed against the interior wall of the vessel, first dilatation balloon 132-1 can be withdrawn. First guide-wire assembly 100-1 is conveniently also withdrawn but may be left in place until the procedure is complete, at the discretion of the user. Second dilatation balloon 132-2 with stent 150 thereon can then be advanced along dual guide-wire assembly 100-2 to insert the stent at the desired location in the vessel. It is not necessary to withdraw and reinsert any guide-wires since the second set of guide-wires is already in place. Being able to place multiple sets of guide-wires in a vessel in a single insertion is an advantage and can reduce the risk of damage to the walls of the blood vessel that may arise from multiple insertions. By using two or more guide-wires bonded together in the manner described above, there is an increase in stiffness without a significant loss of flexibility. This is an advantage of the present invention.

While at least one exemplary embodiment has been presented in the foregoing detailed description, it should be appreciated that a vast number of variations exist. For example, while various different arrangements have been illustrated for forming bonds or joining locations 116, 202 (e.g., 116-1, 116-2, . . . etc.), persons of skill in the art will understand based on the teachings herein that any of the illustrated arrangement may be used in constructing assemblies 100, 200 and further that different arrangements may be used in different locations in the same assembly 100, 200 depending on the needs and preferences of the user. Both discrete and substantially continuous bonding or joining arrangements have been illustrated for assemblies 100, 200 and both are useful, the exact choice depending upon the needs of the user. A combination of discrete and continuous bonding or joining locations may also be used in the same guide-wire assembly. Further, while guide-wires have been mostly illustrated herein as having circular cross-section, this is merely for convenience of explanation and persons of skill in the art will understand that guide-wires of other cross-sectional shape can also be used and are intended to be included in the present invention.

It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing the exemplary embodiment or exemplary embodiments. It should be understood that various changes can be made in the function and arrangement of elements without departing from the scope of the invention as set forth in the appended claims and the legal equivalents thereof.

What is claimed is:

1. An assembly for inserting a bifurcated dilation balloon into a bifurcated channel, the assembly comprising: first and second guide-wires joined to each other at multiple locations by breakable bonds for initially retaining portions of the guide-wires in substantially fixed mutual relationship, said guide-wires each having a diameter and having a length of between 100 cm and 500 cm and a rounded distal tip, said breakable bonds being configured to break as the dilation balloon advances along the guide-wires.

2. The assembly of claim 1 wherein a portion of the first and second guide-wires are held in substantially parallel arrangement by unbroken bonds.

3. The assembly of claim 1 wherein a portion of the breakable bonds are substantially continuous.

4. The assembly of claim 1 wherein the breakable bonds are distributed along a substantial portion of the length of the guide-wires.

5. The assembly of claim 1 wherein a portion of the breakable bonds are formed by shrinkable tubing.

6. The assembly of claim 5 wherein the shrinkable tubing is scored in one or more locations to facilitate breakage thereof to allow the guide-wires to separate as the medical device advances.

7. The assembly of claim 1 wherein a portion of the breakable bonds comprise an adhesive placed between one or more substantially facing locations on the guide-wires.

8. The assembly of claim 1 wherein a portion of the breakable bonds comprise a zipper-like structure for temporarily joining the guide-wires.

9. The assembly of claim 1 further comprising third and fourth guide-wires joined to each other by multiple breakable bonds for initially retaining portions of the third and fourth guide-wires in substantially fixed mutual relationship, wherein said first and second guide-wires and third and fourth guide-wires are further joined by additional breakable bonds, said additional breakable bonds being configured to break as the dilation balloon advances along either the first and second or third and fourth guide-wires.

10. A method for inserting a bifurcated dilation balloon in a channel in a patient, the method comprising: providing a dual guide-wire assembly comprising two guide-wires having diameters and having lengths of between 100 cm and 500 cm and rounded distal tips in the channel wherein the dual guide-wires are breakably bonded to each other at multiple locations along their length, and breaking the multiple bonds while advancing the dilation balloon along the dual guide-wire assembly.

11. The method of claim 10 further comprising releasing the tips of the guide-wires by breaking the last of the multiple bonds with the dilation balloon.

12. The method of claim 10 wherein the providing step comprises providing a dual guide-wire assembly wherein the dual guide-wires are substantially continuously bonded together over a portion of their length.

13. The method of claim 12 wherein the providing step comprises providing a dual guide-wire assembly wherein the dual guide-wires are bonded together over a portion of their length by shrinkable tubing.

14. The method of claim 10 wherein the providing step comprises providing a dual guide-wire assembly wherein the dual guide-wires are at least partly adhesively bonded.

15. The method of claim 10 wherein the providing step comprises providing a dual guide-wire assembly held together in part by a zipper-like structure.

16. The method of claim 10 wherein the dual guide-wire assembly comprises first and second breakably bonded guide-wires and the dilation balloon includes first and second branches suitable for insertion in a bifurcated channel, the method further comprising: threading the first guide-wire through the first branch and threading the second guide-wire through the second branch and the breaking step comprises breaking the multiple bonds when advancing the first and second branches along the guide-wires.

17. A medical device for insertion into a vein or artery, comprising: a dual wire-guide assembly having first and second guide-wires held initially in fixed mutual relationship by breakable attachment means at multiple locations;
  and a dilatation balloon slidably disposed on the dual
    guide-wire assembly which, when advanced toward a
    distal end of the dual guide-wire assembly successively
    breaks said breakable attachment means.

18. The device of claim 17 further comprising a stent disposed on the dilatation balloon.

19. The medical device of claim 17 wherein the dilatation balloon has a main body and first and second branches configured for insertion in a bifurcation of the vein or artery and the first guide-wire runs through the first branch of the dilatation balloon and the second guide-wire runs through the second branch of the dilatation balloon.

20. The medical device of claim 17 wherein the first and second guide-wires have D-shaped cross-sections with flattened portions proximally facing each other.

* * * * *